(12) United States Patent
Umeda (10) Patent No.: US 9,746,453 B2
(45) Date of Patent: Aug. 29, 2017

(54) NUCLEATED-CELL CAPTURING FILTER AND NUCLEATED-CELL PREPARATION METHOD USING SAME

(71) Applicant: KANEKA CORPORATION, Osaka-shi, Osaka (JP)

(72) Inventor: Nobuyoshi Umeda, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 358 days.

(21) Appl. No.: 14/523,405

(22) Filed: Oct. 24, 2014

(65) Prior Publication Data

US 2015/0044767 A1 Feb. 12, 2015

Related U.S. Application Data

(63) Continuation-in-part of application No. PCT/JP2013/061533, filed on Apr. 18, 2013.

(30) Foreign Application Priority Data

Apr. 27, 2012 (JP) ................................ 2012-103688

(51) Int. Cl.
*G01N 33/49* (2006.01)
*C12N 5/07* (2010.01)
(Continued)

(52) U.S. Cl.
CPC .............. *G01N 33/491* (2013.01); *A61M 1/34* (2013.01); *C12N 5/0087* (2013.01); *C12N 5/0642* (2013.01)

(58) Field of Classification Search
CPC ..... A61M 1/34; C12N 5/0087; C12N 5/0642; G01N 33/491
See application file for complete search history.

(56) References Cited

U.S. PATENT DOCUMENTS 5,139,685 A    8/1992  de Castro et al.

FOREIGN PATENT DOCUMENTS

CA    2 766 250 A1    1/2011
JP    8-108069 A    4/1996
(Continued)

OTHER PUBLICATIONS

English translation of International Preliminary Report on Patentability and Written Opinion dated Oct. 28, 2014, in PCT International Application No. PCT/JP2013/061533.
(Continued)

*Primary Examiner* — John Kim
(74) *Attorney, Agent, or Firm* — Birch, Stewart, Kolasch & Birch, LLP (57) ABSTRACT

The present invention has an object to solve the problem in a method for separating nucleated cells from a cell-containing fluid using a cell separation filter. Specifically, the present invention provides a cell separation filter and a method for preparing cells using a cell separation filter, which are capable of reducing unnecessary cell contamination in a nucleated cell fraction without needs of designing non-woven fabrics to suit cell species to be recovered. The present invention also provides a cell separation filter and a method for preparing cells using the filter capable of improving the recovery yield of nucleated cells. The present invention provides a cell separation filter comprising: a container having an inlet and an outlet, an adsorbent filled in the container, and a partition having an opening, the partition separating the adsorbent. The present invention also provides a method for preparing nucleated cells including the steps of: introducing a cell-containing fluid through the inlet of the cell separation filter to contact the cell-containing fluid with the adsorbent; and recovering a nucleated cell fraction from the filter.

20 Claims, 3 Drawing Sheets

(51) Int. Cl.
    *C12N 5/00* (2006.01)
    *A61M 1/34* (2006.01)
    *C12N 5/0787* (2010.01)

(56) References Cited

FOREIGN PATENT DOCUMENTS

| | | |
|---|---|---|
| JP | 2001-178 A | 1/2001 |
| JP | 2001-136956 A | 5/2001 |
| JP | 2003-274923 A | 9/2003 |
| JP | 2004-215875 A | 8/2004 |
| JP | 2004-329034 A | 11/2004 |
| JP | 2005-535425 A | 11/2005 |
| JP | 2009-207381 A | 9/2009 |
| WO | WO 2006/093205 A1 | 9/2006 |

OTHER PUBLICATIONS

Nakano-Doi et al., "Bone Marrow Mononuclear Cells Promote Proliferation of Endogenous Neural Stem Cells Through Vascular Niches After Cerebral Infarction," Stem Cells (2010), vol. 28, pp. 1292-1302.

Taguchi et al., "Therapeutic Angiogenesis by Autologous Bone-marrow Transplantation in a General Hospital Setting," Eur. J. Vasc. Endovasc. Surg. (2003), vol. 25, pp. 276-278.

NUCLEATED-CELL CAPTURING FILTER AND NUCLEATED-CELL PREPARATION METHOD USING SAME

CROSS REFERENCE TO RELATED APPLICATIONS

This application is a Continuation-in-Part of PCT International Application No. PCT/JP2013/061533 filed on Apr. 18, 2013, which designated the United States, and which claims priority on Japanese Patent Application No. 2012-103688 filed on Apr. 27, 2012. Both of these applications are hereby expressly incorporated by reference herein in their entirety.

TECHNICAL FIELD

The present invention relates to a cell separation filter capable of efficiently recovering a nucleated cell fraction from a cell-containing fluid and a method for preparing nucleated cells using the filter.

BACKGROUND ART

In recent years, a certain treatment style has been widely spread, that is, a treatment style which involves treating a cell-containing fluid typically such as peripheral blood, bone marrow, umbilical cord blood, or tissue extracts, to isolate only cell fractions which are effective in the treatment, and then administering the cell fractions to a patient to enhance therapeutic effects, whereas unnecessary components are removed without administration, thereby reducing side effects more efficiently. An example is a hematopoietic stem cell transplant for the treatment of leukemia or solid cancers. During the transplant, only cells effective in the treatment (nucleated cells, including hematopoietic stem cells), which are separated from bone marrow or peripheral blood by removing red blood cells for purification, are administered to patients. Umbilical cord blood banking requires cells to be cryopreserved before use. Thus, it also requires separation and purification of nucleated cells to prevent red blood cell hemolysis, which may occur during cryopreservation. Further, transplantation of mononuclear cell fractions of bone marrow, umbilical cord blood, or peripheral blood has been used in clinical practice for the treatment of ischemic diseases, such as cerebral infarction, myocardial infarction, and limb ischemia. Such mononuclear cell fractions are rich in stem cells, typically such as mesenchymal stem cells, hematopoietic stem cells, and endothelial progenitor cells, and it is believed that the stem cells promote angiogenesis or nerve regeneration, thereby producing a therapeutic effect. Meanwhile, it is believed that granulocytes can cause side effects, such as inflammation, to reduce the therapeutic effect. Therefore, only cells which are effective in the treatment (a group of mononuclear cells, including stem cells) are separated from bone marrow or peripheral blood by removing granulocytes for purification, and administered to a patient.

For example, Taguchi et al. demonstrate that transplantation of bone marrow mononuclear cells containing CD34 positive cells to patients who suffer Buerger's disease (one of peripheral arterial occlusive diseases) accelarates angiogenesis and therefore can be an effective way to treat Buerger's disease (See Non Patent Literature 1). Nakano-Doi et al. have also reported that transplantation of bone marrow-derived mononuclear cells is effective as the treatment for patients who suffer acute ischemic diseases, typically such as cerebral infarction, or ischemic heart diseases (See Non Patent Literature 2).

Typical examples of a method for separation and purification of such nucleated cells or mononuclear cells include centrifugation, and density-gradient centrifugation using an isolation medium, typically such as the Ficoll solution. The density-gradient centrifugation method, however, has some disadvantages. For example, the method has a large physical impact on cells, and needs complicated operations and operations in an open system. Thus, this method requires a large facility, called cell processing center (CPC), to perform cell therapy.

Based on the above situation, as a cell separation method allowing simple operation in a closed system, a nucleated cell separation method using a device including non-woven fabrics is disclosed (see Patent Literature 1). Also, the following methods are disclosed: a method of removing leukocytes using a device in which non-woven fabrics that are processed by forming pores with a specific pore-area ratio to suppress clogging are laminated between two different filters (see Patent Literature 2); a method of efficiently recovering mononuclear cells using a cell separation filter that selectively captures granulocytes (see Patent Literature 3). However, these methods require non-woven fabrics, which originally lack versatility, to be designed to suit target cells in order to improve a recovery yield or reduce unnecessary cell contamination.

Considering the above disadvantages such as impacts on cells due to centrifugation, requirement for complicated operations, and the risk of contamination, a separation method using a cell separation filter which has a structure in a laminate of non-woven fabrics is preferred. Unfortunately, to improve performance of non-woven fabrics, the cell separation filter becomes poor in versatility, and it is only suitable for a specific cell. Thus, non-woven fabrics need to be developed to suit respective cell species, which will be disadvantageous. The solution for such problems has not yet been found so far.

CITATION LIST

Patent Literature

Patent Literature 1: JP 2004-329034 A
Patent Literature 2: JP 2004-215875 A
Patent Literature 3: WO 06/093205

Non Patent Literature

Non Patent Literature 1: A. Taguchi. et al., Eur. J. Vasc. Endovasc. Surg. 2003, 25, 276-278
Non Patent Literature 2: A. Nakano-Doi et al., Stem Cells. 2010, 28, 1292-1302

SUMMARY OF INVENTION

Technical Problem

The present invention has an object to solve the problem in a method for separating nucleated cells from a cell-containing fluid using a cell separation filter. Specifically, the present invention provides a cell separation filter and a method for preparing cells using a cell separation filter, which are capable of reducing unnecessary cell contamination in a nucleated cell fraction without needs of designing non-woven fabrics to suit cell species to be recovered. The present invention also provides a cell separation filter and a method for preparing cells using the cell separation filter, which are capable of improving the recovery yield of nucleated cells.

Solution to Problem

The present inventor has paid an attention on the structure of a cell separation filter, and has intensively studied to solve the above problems. As a result, the inventors have unexpectedly found that an adsorbent filled in a container which is equipped with an inlet and an outlet and formation of partitions separating the adsorbent in the filter enable to improve the recovery yield of nucleated cells and reduce unnecessary-cell contamination even if the adsorbent is not optimized. The inventors have unexpectedly found that the cell separation filter is sufficiently versatile in that modification of non-woven fabrics to suit cell species is not required. Thus, the present invention has been completed.

That is, the present invention relates to a cell separation filter including:

a container having an inlet and an outlet,
an adsorbent filled in the container, and
a partition having an opening for separating the adsorbent, the container being divided into two or more rooms by the partition.

The value (S1)/(S2) is preferably not less than 0.006 but not more than 0.44, where the (S1) is an area of the opening of the partition, the (S2) is a cross-sectional area of the filter.

Preferably, the (S1) is 1.2 to 625 mm$^2$ and/or (S2) is 75 to 2500 mm$^2$.

The value (T)/(R) is preferably not less than (r)/(R) but not more than 0.79, where the (R) is the shortest distance from the center to the edge of the container in the cross-section of the filter, the (T) is the farthest distance from the center to the edge of the opening of the partition in the cross-section of the filter, the (r) is the shortest distance from the center of the opening to the edge of the opening.

The adsorbent is preferably composed of non-woven fabrics.

The adsorbent is preferably composed of porous cellulose particles.

The adsorbent preferably comprises a compound having a log P value of not less than 2.50 immobilized on the porous cellulose particles. P is an octanol-water partition coefficient.

The adsorbent preferably comprises a tryptophan derivative and a polyanionic compound immobilized on the porous cellulose particles.

The present invention also relates to a method for preparing nucleated cells involving the steps of:

(a) introducing a cell-containing fluid through the inlet of the cell separation filter to contact the cell-containing fluid with the adsorbent; and (b) recovering a nucleated cell fraction from the cell separation filter.

In the step (b), the nucleated cell fraction is preferably recovered by introducing a solution for recovering the fraction through the inlet of the filter.

In the step (b), the nucleated cell fraction is preferably recovered by introducing a solution for recovering the fraction through the outlet of the filter.

The method preferably comprises after the step (b): passing the nucleated cell fraction through a dialyzer; and recovering the nucleated cell fraction.

The nucleated cell fraction is preferably a mononuclear cell fraction.

Granulocytes are preferably selectively removed from the cell-containing fluid.

At least one selected from the group consisting of low-density lipoproteins, fibrinogen, and β2-microglobulin (β2M) is preferably removed from the cell-containing fluid.

The value (M)/(G) is preferably not less than 5.3, where (M) is a recovery yield of mononuclear cells, and (G) is a recovery yield of the granulocytes.

Advantageous Effects of Invention

According to the present invention, the partition formed in the cell separation filter slows down the flow rate of a cell-containing fluid in the cell separation filter, thereby extending the time of contact between the cell-containing fluid and adsorbent. Furthermore, the probability of leakage of cells, which are to be captured by the adsorbent but pass through the edge of the container without passing through the adsorbent, is reduced. Accordingly, a nucleated cell fraction can be efficiently captured and recovered from the cell-containing fluid. As a result of the improved recovery yield of the nucleated cells, the present invention enables efficient preparation of a necessary amount of nucleated cell fraction from a small amount of cell-containing fluid, and is therefore expected to reduce burdens on donors. In addition, the cell separation filter including an adsorbent for capturing granulocytes filled therein enables recovery of a high mononuclear cell fraction with a higher granulocyte removal rate than conventional one.

DESCRIPTION OF EMBODIMENTS

Figure 1:
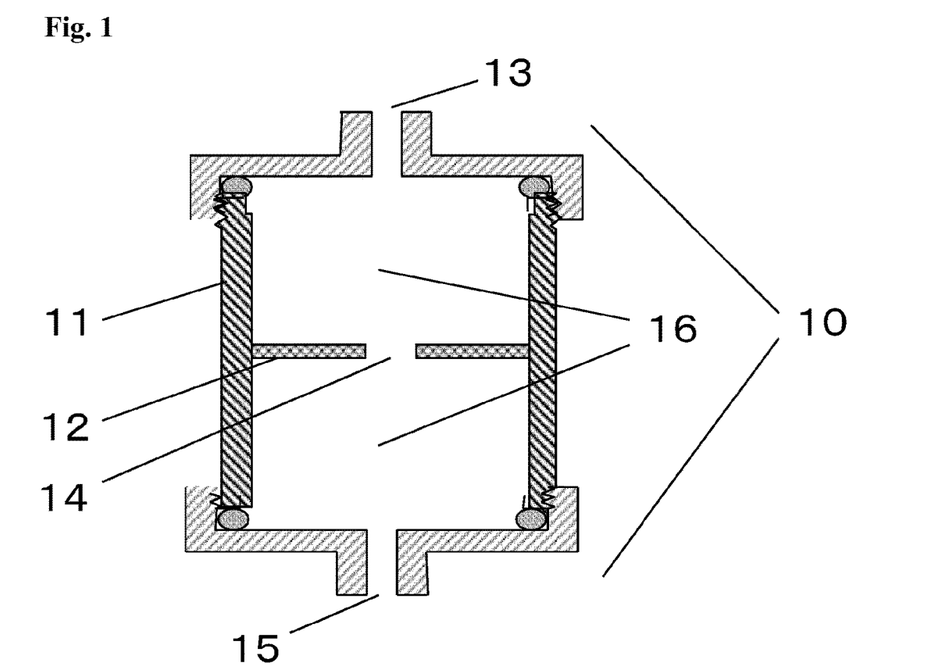
FIG. 1 is a vertical cross-section of a cell separation filter which is provided with a partition.

The present invention is described in detail below. As shown in FIG. 1, the cell separation filter of the present invention includes a container which is provided with an inlet and an outlet, and an adsorbent filled in the container. The shape and the size of the container are not particularly limited. Examples of the shape of the container include a round column, a square column, an elliptical column, and a diamond-shaped column.

The container used in the cell separation filter may be made of any structural materials. Specific examples of the structural materials of the container include nonreactive polymers, biocompatible metals and alloys, and glass.

Examples of the nonreactive polymers include acrylonitrile polymers (e.g. acrylonitrile butadiene styrene terpolymers), halogenated polymers (e.g. polytetrafluoroethylene, polychlorotrifluoroethylene, tetrafluoroethylene-hexafluoropropylene copolymers, polyvinyl chloride), polyamides, polyimides, polysulfone, polycarbonate, polyethylene, polypropylene, polyvinyl chloride-acrylic copolymers, polycarbonate/acrylonitrile-butadiene-styrene, polystyrene, and polymethylpentene.

Examples of the biocompatible metals and alloys include stainless steel, titanium, platinum, tantalum, gold, and alloys of these, gold-plated ferroalloys, platinum-plated ferroalloys, cobalt chromium alloys, and titanium nitride-coated stainless steel.

Preferred structural materials are materials having sterilization resistance, such as polypropylene, polyvinyl chloride, polyethylene, polyimide, polycarbonate, polysulfone, and polymethylpentene.

Examples of the adsorbent of the present invention include non-woven fabrics and water-insoluble porous supports.

The non-woven fabrics in the present invention may be made of any materials. Examples of the materials include, but are not particularly limited to, materials having sterilization resistance or safety for cells, including synthetic polymers such as polyethylene terephthalate, polybutylene terephthalate, polyethylene, high-density polyethylene, low-density polyethylene, polyvinyl alcohol, vinylidene chloride, rayon, vinylon, polypropylene, acrylics (polymethyl methacrylate, polyhydroxyethyl methacrylate, polyacrylic nitrile, polyacrylic acid, polyacrylate), nylon, polyimide, aramid (aromatic polyamide), polyamide, cupra, carbon, phenol, polyester, pulp, hemp polyurethane, polystyrene, and polycarbonate; natural polymers such as agarose, cellulose, cellulose acetate, chitosan, and chitin; inorganic materials such as glass; and metals. Preferred are polyethylene terephthalate, polybutylene terephthalate, polypropylene, acrylics, nylon, and polyurethane, which are highly capable of capturing cells. More preferred are polyethylene terephthalate and nylon, which have high ability of capturing nucleated cells. Fibers formed from a combination of two or more types of materials may be fibers in which each fiber is formed of materials different from one another in their components, splittable fibers in which different components are splitted, or a composite formed of fibers consisting of a plurality of different components. The "composite" herein is not particularly limited, and examples thereof include fibers formed of two or more types of fibers in a mixed state, and fibers in which each fiber is made of a single material and the fibers are bonded together. Molecules having affinity with specific cells, such as proteins, peptides, amino acids, and saccharides, may be immobilized on fibers.

To the non-woven fabrics, it is preferable to impart hydrophilicity. The non-woven fabrics with hydrophilicity suppress non-specific capture of cells other than nucleated cells and allow a biological fluid or a treated solution of body tissues to uniformly pass through the cell separation filter, and thus may contribute to the improvement of the performance of the filter and the recovery yield of necessary cells. Examples of the treatments of imparting hydrophilicity include a method of allowing a water-soluble polyhydric alcohol, a polymer containing a hydroxyl group, a cationic group, or an anionic group, or a copolymer of such a polymer (e.g., hydroxyethyl methacrylate, dimethylaminoethyl methacrylate, or the copolymers thereof) to be adsorbed; a method of allowing a water-soluble polymer (e.g., polyethylene glycol, polyvinyl pyrrolidone, polyvinyl alcohol) to be adsorbed; a method of immobilizing a hydrophilic polymer on a hydrophobic membrane; a method of irradiating a cell separation filter with electrons; a method of irradiating a cell separation filter in a moisture state with radiation to cross-link a hydrophilic polymer for insolubilization; a method of sulfonating the surface of a hydrophobic membrane; a method of preparing a membrane from a mixture of a hydrophilic polymer and a hydrophobic polymer dope; a method of introducing hydrophilic groups on the surface of a membrane by a treatment using an aqueous alkaline solution (e.g., NaOH, KOH); a method of immersing a hydrophobic porous membrane in an alcohol, next treating the membrane with an aqueous water-soluble polymer solution, then drying the membrane, and finally heat-treating or radiation processing the membrane for insolubilization; and a method of allowing a surface active substance to be adsorbed. Examples of the hydrophilic polymer include polyvinyl pyrrolidone, polyvinyl alcohol, polyethylene glycol, ethylene-vinyl alcohol copolymers, and water-soluble polyhydric alcohols.

Examples of the proteins to be immobilized on the non-woven fabrics include, but are not particularly limited as long as they have affinity with specific cells, fibronectin, laminin, vitronectin, and collagen. Examples of the saccharides to be immobilized on the non-woven fabrics include, but are not particularly limited as long as they have affinity with cells, polysaccharides such as cellulose, chitin, and chitosan; and oligosaccharides such as mannose, glucose, galactose, and fucose.

According to the present invention, non-woven fabrics which are different from one another in their materials, mass per unit area ($g/m^2$), maximum pore size (m), fiber diameter (m), and air permeability ($mL/cm^2/sec$) may be laminated in respective rooms divided by the partition.

The maximum pore size (in units of meters) of the non-woven fabrics to be used in the cell separation filter may be determined as follows. First, non-woven fabrics are set in a device for measuring bubble point of a filter disc, next ethanol is poured from the upper portion of the device to a certain level, and then compressed air is introduced from the lower portion to apply a pressure. Then, the pressure when a first bubble is observed on the surface of the non-woven fabrics through an ethanol phase is read from a digital manometer as a bubble point pressure. Finally, the bubble point pressure is converted by the following equation:

$$\text{(Maximum pore size)} = 4 \times \text{(Surface tension of ethanol (in units of N/m))} \times \cos\theta / \text{(Bubble point pressure (in units of Pa))}.$$

Thus, the maximum pore size is determined. In the equation, the $\theta$ (in units of radians) is determined by first preparing a smooth film from a polymer compound, which is a main component of the non-woven fabrics, next forming a liquid droplet on the film using a microsyringe in a horizontal state, and then measuring the contact angle between the film and the droplet as the $\theta$ at room temperature. In cases where the polymer compound is soluble in an organic solvent, the contact angle may be measured using a cast film prepared on a flat plate using a solution of the polymer compound.

The air permeability of the non-woven fabrics of the present invention may be determined as follows: first, non-woven fabrics are set in a Frazier air permeability tester, next an induced draft fan is controlled such that an inclined manometer reads a pressure of 125 Pa, and then the amount of air passing through the sample is determined as an air permeability based on the pressure read by a vertical manometer at that time and the kind of used orifice with reference to a table attached to the tester. The fiber diameter of the non-woven fabrics of the present invention can be determined by first photographing the non-woven fabrics with a scanning electron microscope; next, fiber diameters of 30 or more points chosen at random are measured; then calculating the diameters of fibers based on a magnification scale of the photograph; and finally averaging the calculated diameters.

Typical examples of the water-insoluble porous supports of the present invention include organic supports composed of polysaccharides such as cellulose, cellulose acetate, and dextrin; and synthetic polymers such as polystyrene, styrene-divinyl benzene copolymers, polyacrylamide, polyacrylic acid, polymethacrylic acid, polyacrylic acid esters, polymethacrylic acid esters, and polyvinyl alcohol. These may have a coating layer made of a hydroxy group-containing polymeric material such as hydroxyethyl methacrylate, or made of a graft copolymer such as a copolymer of a polyethylene oxide chain-containing monomer and another polymerizable monomer. Among these, cellulose and synthetic polymers such as polyvinyl alcohol are preferred for practical use because an active group is easily introduced into the surfaces of such supports. In particular, cellulose is most preferably used as the support.

In cases where molecules to be removed by the cell separation filter of the present invention are β2-microglobulin (β2M), the porous water-insoluble support preferably is a porous water-insoluble support on which a compound having a log P value (P is an octanol-water partition coefficient) of not less than 2.50 is immobilized. The log P value is more preferably not less than 2.70, and still more preferably not less than 2.90. β2-microglobulin may be removed by the cell separation filter of the present invention in such a way that β2-microglobulin is adsorbed by hydrophobic interaction between β2-microglobulin and atom groups introduced by immobilizing a compound having a log P value of not less than 2.50 on the porous water-insoluble support. Therefore, a compound having a log P value of less than 2.50, whose hydrophobicity is too small, may not exert adsorption of the β2-microglobulin. Compounds having a log P value of not less than 2.50 are preferably compounds having a C7-C20 hydrocarbon site, and more preferably compounds having a functional group capable of binding with cellulose. Examples of the compounds having a functional group capable of binding with cellulose include unsaturated hydrocarbons, alcohols, amines, thiols, carboxylic acids, and their derivatives, halides, aldehydes, isocyanatos, oxirane ring-containing compounds such as glycidyl ether, and halogenated silanes.

In cases where molecules to be removed by the cell separation filter of the present invention are low-density lipoprotein and fibrinogen, the porous water-insoluble support preferably is the porous water-insoluble support on which a tryptophan derivative and a polyanionic compound are immobilized. A polyanionic compound is a compound having a plurality of anionic functional groups in the molecule. The anionic functional group herein refers to a neutral pH and negatively charged functional group such as a carboxyl group, a sulfonic acid group, a sulfate group, and a phosphoester group. Among these, a carboxyl group, a sulfonic acid group, and a sulfate group are preferred in view of their adsorption ability. In particular, a sulfate group is preferred because of its better adsorption ability. Typical examples of the polyanionic compound include synthetic polyanionic compounds such as polyacrylic acid, polyvinyl sulfonic acid, polystyrene sulfonic acid, polyglutamic acid, polyaspartic acid, polymethacrylic acid, polyphosphoric acid, and styrene-maleic acid copolymers; synthetic acid polysaccharides such as dextran sulfate and carboxymethylcellulose; sulfate group-containing biological mucopolysaccharides such as chondroitin sulfate, dermatan sulfate, and keratan sulfate; N-sulfonic acid group- and sulfate group-containing acid mucopolysaccharides such as heparin and heparan sulfate; anionic functional group-containing biological polysaccharides such as chondroitin and phosphomannan; and biological nucleic acid such as deoxyribonucleic acid and ribonucleic acid. Among these compounds, synthetic compounds are more practically used than biological compounds without any change because synthetic compounds are prepared at low costs with high purity and the amount of the anionic functional groups to be introduced can be controlled. For these points, synthetic polyanionic compounds such as polyacrylic acid, polyvinyl sulfate, polyvinyl sulfonic acid, polystyrene sulfonic acid, polyglutamic acid, polyaspartic acid, polymethacrylic acid, polyphosphoric acid, and styrene-maleic acid copolymers; and synthetic acid polysaccharides such as dextran sulfate and carboxymethylcellulose are preferably used. In particular, polyacrylic acid, polystyrene sulfonic acid, and dextran sulfate are particularly preferred because of their low costs, and dextran sulfate is more particularly preferred in view of safety. The tryptophan derivatives of the present invention refer to tryptophan esters such as tryptophan, tryptophan ethyl ester, and tryptophan methyl ester; and compounds having a structure similar to an indole ring-containing tryptophan, such as tryptamine and tryptophanol. These tryptophan derivatives may be in L, D, or DL form, or may have a form of a mixture thereof. Further, two or more tryptophan derivatives may be used in combination. Among these tryptophan derivatives, tryptophan is preferred in view of safety. In particular, L-tryptophan is most preferred for practical use because it is a natural amino acid and is available at low costs, and is rich in data on safety.

The log P value is a parameter of hydrophobicity of a compound. A typical octanol-water partition coefficient P is determined as follows. First, a compound is dissolved in octanol (or water), and to the solution is added water (or octanol) in a quantity equal to the first used octanol (or water). The resulting solution is shaken for 30 minutes with a Griffin flask shaker produced by Griffin & George Ltd. Then, centrifugation is performed at 2000 rpm for 1 to 2 hours. The concentration of the compound in each of the octanol phase and the aqueous phase is spectroscopically measured or the GLC concentration thereof is measured. P is determined by using the following equation.

$$P = C_{oct}/C_w$$

($C_{oct}$: concentration of the compound in the octanol phase, $C_w$: concentration of the compound in the aqueous phase)

Many researchers have actually measured log P values of various compounds. The actual measurement values are tabulated by C. Hansch et al. (see PARTITION COEFFICIENTS AND THEIR USES; Chemical Reviews), Volume 71, page 525, 1971).

Regarding compounds in which no actual measurement value is determined, see values (Σf) calculated using a hydrophobic fragmental constant f, shown in "THE HYDROPHOBIC FRAGMENTAL CONSTANT)", (ElsevierSci. Pub. Com., Amsterdam) (1977) written by R. F. Rekker. A hydrophobic fragmental constant is determined by statistical processing of many actual measurement values of log P, and shows the hydrophobicity of various fragments. The log P value is reported to approximately coincide with a sum of values f of fragments composing a compound. In the present invention, log P includes Σf.

Figure 2:
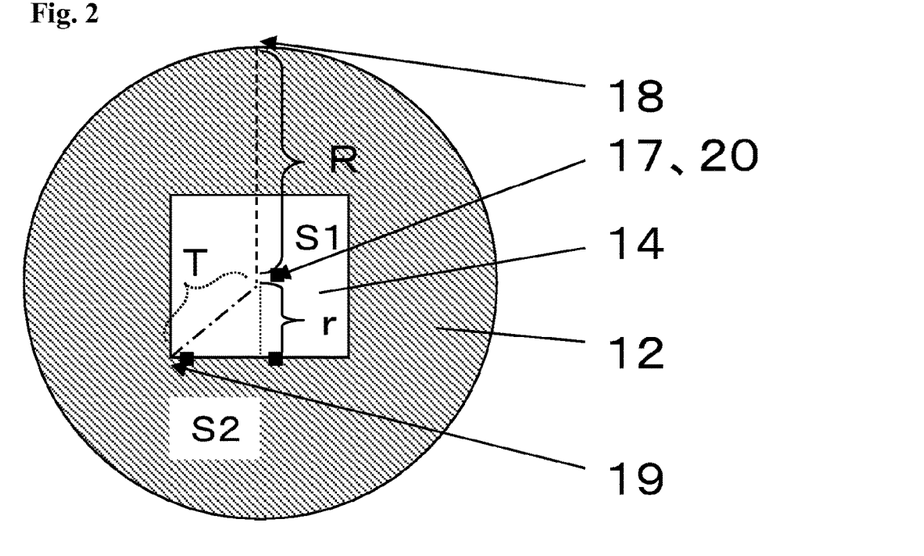
FIG. 2 is a transverse cross-section of a cell separation filter which is provided with a partition having one opening.
Figure 3:
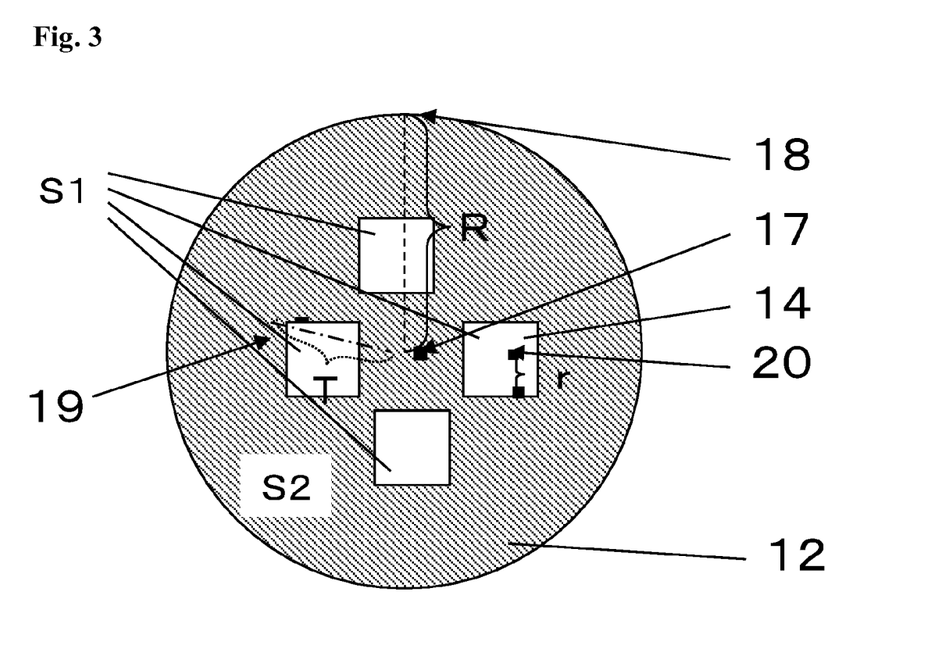
FIG. 3 is a transverse cross-section of a cell separation filter which is provided with a partition having two or more openings.

The cell separation filter of the present invention has the following features (1) to (3) so that the filter efficiently captures nucleated cells:

(1) a partition or partitions is/are installed in the filter to separate the adsorbent, as shown in FIGS. 1 to 3,
(2) the partition(s) has(have) at least one opening, and
(3) the space in the filter is divided by the partition(s) into two or more rooms.

The partition of the present invention is arranged in a direction perpendicular to the direction of the flow of the treated solution, and is made of a material prohibiting cells from passing through it. Therefore, cells are not captured by the partition even if they are in contact with the partition.

Cells move to another room which is divided by the partition through at least one opening of the partition.

The partition of the present invention may be made of any structural material or film-like sheet as long as it does not allow cells to pass through it. A rigid structural material or sheet is preferably used in order to avoid the partition from deformed or broken by pressure on passing cell-containing fluid or recovery solution. Further, the partition may be designed such that only the partition is detachable from the cell separation filter without leakage of a liquid contained in the filter, or that the area of the opening can be changed.

Examples of the structural material that forms the partition include nonreactive polymers, biocompatible metals and alloys, and glass.

Examples of the nonreactive polymers include acrylonitrile polymers (e.g. acrylonitrile butadiene styrene terpolymers), halogenated polymers (e.g., polytetrafluoroethylene, polychlorotrifluoroethylene, tetrafluoroethylene-hexafluoropropylene copolymers, polyvinyl chloride), polyamides, polyimides, polysulfone, polycarbonate, polyethylene, polypropylene, polyvinyl chloride-acrylic copolymers, polycarbonate/acrylonitrile-butadiene-styrene, polystyrene, and polymethylpentene.

Examples of the biocompatible metals and alloys include stainless steel, titanium, platinum, tantalum, gold, and alloys of these, gold-plated ferroalloys, platinum-plated ferroalloys, cobalt chromium alloys, and titanium nitride-coated stainless steel.

Preferred examples of the structural material that forms the partition include materials having sterilization resistance, such as polypropylene, polyvinyl chloride, polyethylene, polyimides, polycarbonate, polysulfone, and polymethylpentene. A material of the film-like sheet is preferably a material having sterilization resistance, such as polypropylene, polyvinyl chloride, polyethylene, polyimides, polycarbonate, polysulfone, and polymethylpentene.

The partition of the present invention is provided with at least one opening for allowing cells to pass through the partition. The opening is preferably provided in the center of the partition in view of cell capturing efficiency. The (S1) illustrated in each of FIGS. 2 and 3 is the area of the opening of the partition. The (S2) is the cross-sectional area of the filter. The area (S1) of the opening can be obtained from the radius of the opening when the opening has a circular shape, or obtained from the length of the side of the opening or the distance from the center to a corner of the opening when the opening has a polygonal shape. In cases where a plurality of openings is provided with the partition, the (S1) is obtained as a sum of the areas of the openings determined as mentioned above. The (S1) is preferably not less than 1.2 mm$^2$ and not more than 625 mm$^2$, more preferably not less than 1.6 mm$^2$ and not more than 575 mm$^2$, and still more preferably not less than 2.8 mm$^2$ and not more than 525 mm$^2$. If the (S1) is less than 1.2 mm$^2$, a cell-containing fluid or recovery solution may generate a high pressure in the vicinity of the opening of the partition when passing, which tends to damage cells. On the contrary, if an opening with the (S1) is more than 625 mm$^2$, it may be so large that the recovery yield of the nucleated cells tends to be reduced.

The cross-sectional area (S2) of the filter is an area of the cross-section in the plane in which the opening(s) of the filter is/are present. The cross-sectional area (S2) can be obtained from the radius of the filter when the cross-section has a circular shape, or obtained from the length of the side of the cross-section or the distance from the center to a corner of the cross-section when the cross-section has a polygonal shape. The (S2) is preferably not less than 75 mm$^2$ and not more than 2500 mm$^2$, more preferably not less than 100 mm$^2$ and not more than 2300 mm$^2$, and still more preferably not less than 175 mm$^2$ and not more than 2100 mm$^2$. If the (S2) is less than 75 mm$^2$, a cell-containing fluid or recovery solution may generate a high pressure in the vicinity of an opening of the partition when passing, which tends to damage cells. On the other contrary, if the (S2) is more than 2500 mm$^2$, the volume of the container may be so large that the recovery yield of the nucleated cells tends to be reduced.

Regarding the relationship between the (S1) and the (S2) in the present invention, (S1)/(S2) is preferably not less than 0.006 and not more than 0.44, more preferably not less than 0.01 and not more than 0.3, and still more preferably not less than 0.016 and not more than 0.25. If (S1)/(S2) is less than 0.006, a cell-containing fluid or recovery solution may generate a high pressure in the vicinity of an opening of the partition when passing, which tends to damage cells. If (S1)/(S2) is more than 0.44, the recovery yield of the nucleated cells tends to be reduced.

As shown in FIGS. 2 and 3, (T)/(R) is preferably not less than (r)/(R) and not more than 0.79, where the shortest distance from the center to the edge of the container in the cross-section of the filter is the (R), the distance from the center of the cross-section of the filter to the point of the opening of the partition farthest from the center of the cross-section of the filter is the (T), and the shortest distance from the center of the opening to the edge of the opening in the partition is the (r). In cases where a plurality of openings are provided with the partition, the shortest distance from the center of the opening closest to the center of the cross-section of the filter to the edge of the opening is the (r). The upper limit of (T)/(R) is more preferably not more than 0.70, and still more preferably not more than 0.64. If the upper limit of (T)/(R) is more than 0.79, the edge of the opening is close to the edge of the container, or, if a plurality of openings are present, they may be localized in the region close to the edge of the container. Therefore, a cell-containing fluid or recovery solution is likely to unevenly flow when passing through the adsorbent, and does not spread over the whole of the filter, which tends to reduce the cell capturing efficiency.

The shape of the cross-section of the filter is not particularly limited, and examples of the shape include circular, rectangular, and square shapes. The shortest distance (R) from the center to the edge of the container in the cross-section of the filter is the radius of the cross-section of the filter when the cross-section has a circular shape, is the half the length of the short side of the cross-section of the filter when the cross-section has a rectangular shape, and is the half the length of the side of cross-section of the filter when the cross-section has a square shape.

The (R) is preferably not less than 5 mm and not more than 25 mm, and more preferably not less than 7.5 mm and not more than 22.5 mm. If the (R) is less than 5 mm and (S1)/(S2) is not more than 0.44, the area of the opening is too small. Therefore, a cell-containing fluid or recovery solution generates a high pressure in the vicinity of the opening of the partition when passing, which tends to damage cells. On the contrary, if a container has the (R) of more than 25 mm, the volume of the container may be so large that the cell recovery tends to be reduced.

The shape of the opening of the partition is not particularly limited, and may be, for example, a circular, rectangular, square, or ellipse shape. The shortest distance (r) from the center of the opening to the edge of the opening of the partition is determined as the radius of the opening when the opening has a circular shape, determined as the half the length of the short side of the opening when the opening has a rectangular shape, or determined as the half the length of the side of the opening when the opening has a square shape. The area (S1) of the opening of the partition is limited depending on the area (S2) of the cross-section of the filter. Therefore, the (r) is preferably not less than 0.4 mm and not more than 16 mm, more preferably not less than 0.5 mm and not more than 14 mm, and still more preferably not less than 0.7 mm and not more than 12 mm. If the opening has an (r) of less than 0.4 mm, the area of the opening may be so small that a cell-containing fluid or recovery solution may generate a high pressure in the vicinity of the opening of the partition when passing, which tends to damage cells. If the opening has an (r) of more than 16 mm, the area of the opening may be so large that the edge of the opening of the partition may be close to the edge of the container. Therefore, a cell-containing fluid or recovery solution is likely to unevenly flow when passing through the adsorbent, and may not spread over the whole of the filter, which tends to reduce cell capturing efficiency.

The distance (T) from the center of the cross-section of the filter to the point of the edge of the opening farthest from the center in the filter is limited depending on the (R) and the (r). The (T) is calculated according to the preferable value of (R) and (r) that can be appropriately used. The (T) is preferably not less than 0.4 mm and not more than 19 mm, and more preferably not less than 0.7 mm and not more than 17 mm.

The shortest distance (R) from the center of the cross-section of the filter to the edge of the container in the cross-section of the filter, the farthest distance (T) from the center of the cross-section of the filter to the edge of the opening of the partition in the cross-section of the filter, and the shortest distance (r) from the center of the opening of the partition to the edge of the opening of the partition in the present invention can be determined by measuring the distance from the center of the cross-section of the filter in a face including an opening of the partition, or the distance from the center of an opening of the partition in a plane, in which the opening is present, with a ruler or a caliper or other tools or drawing software such as a CAD or Illustrator.

The number of openings of the partition is not particularly limited. Also, the number of partitions in the cell separation filter is not particularly limited, and is preferably not more than 15, more preferably not more than 10, and still more preferably not more than 5. The cell capturing efficiency is more improved as the number of partitions for dividing the space increases, but the cell recovery yield after recovery tends to be reduced. Therefore, it is preferred that the number of the partitions is appropriately controlled according to the intended purpose of the cell separation filter. For example, in cases where the filter is used for removing granulocytes, the granulocyte removing performance is improved by increasing the number of partitions. However, if the number of partitions exceeds 15, the mononuclear cell recovery yield tends to be remarkably lowered. Accordingly, the number of partitions is preferably not more than 15.

The method for preparing nucleated cells of the present invention includes the following steps (a) and (b):
(a) introducing a cell-containing fluid through the inlet of the cell separation filter to contact the cell-containing fluid with the adsorbent; and
(b) recovering a nucleated cell fraction from the cell separation filter.

The cell-containing fluid of the present invention may be a biological fluid that contains cells such as peripheral blood, bone marrow, umbilical cord blood, menstrual blood, or tissue extract; solutions of these biological fluids diluted with physiological saline, a Ringer's solution containing a divalent cation such as a calcium ion or a magnesium ion, a medium such as RPMI, MEM, IMEM, or DMEM, which has been used in a cell culture, and a phosphate buffer such as PBS; or a fluid obtained by roughly separating the cells from a biological fluid. The animal species are not particularly limited as long as they are mammals such as humans, bovines, mice, rats, swine, monkeys, dogs, and cats. The cell-containing fluid may contain an anti-coagulant. Examples of the anti-coagulant include, but are not particularly limited to, heparin, low-molecular-weight heparin, Futhan (nafamostat mesilate, citric acid anticoagulants such as EDTA, an ACD (acid-citrate-dextrose) solution, and a CPD (citrate-phosphate-dextrose) solution. The storage conditions of the cell-containing fluid are not particularly limited, as long as the conditions do not affect the intended uses thereof.

The nucleated cells of the present invention are not particularly limited as long as they have a nucleus, and examples of the nucleated cells include mononuclear cells, leukocytes, granulocytes, neutrophils, eosinophils, basophils, erythroblasts, myeloblasts, promyelocytes, myelocytes, metamyelocytes, lymphocytes, monocytes, macrophages, T lymphocytes, B lymphocytes, NK cells, NK/T cells, dendritic cells, ltinucleatedgiant cells, epithelial cells, endothelial cells, mesenchymal cells, mesenchymal stem cells, hematopoietic stem cells, ES cells, iPS cells, and stem cells. The nucleated cell fraction of the present invention is a fraction containing nucleated cells, and the mononuclear cell fraction is a fraction containing mononuclear cells. The stem cell of the present invention is a cell having multipotential and ability to self-renew and separated from a biological fluid. Granulocytes, which are cells containing a nucleus, cause side effects such as inflammation when transplanted into a patient, and reduce the therapeutic effects. Therefore, low concentration of the granulocyte in the nucleated cell fraction is preferable.

The mesenchymal stem cells in the present invention differentiate into osteoblasts, chondrocytes, vascular endothelial cells, cardiomyocytes, or cementoblast cells such as adipose tissue and periodontal tissue cells, periodontal ligament fibroblast cells by adding a differentiation-inducing factor. Further, hematopoietic stem cells differentiate into blood cells such as leukocytes, lymphocytes, neutrophils, eosinophils, basophils, granulocytes, monocytes, macrophage, red blood cells, platelets, megakaryocytes, or dendritic cells.

The step of recovering a nucleated cell fraction from the cell separation filter of the present invention is a step of recovering a fraction containing many nucleated cells that are obtained through the filter. In the step, a nucleated cell fraction may be recovered according to the type of the cell separation filter.

In cases where the adsorbent filled in the filter has affinity with cells, molecules, or contaminants to be removed, a cell-containing fluid is introduced through the inlet of the filter to contact the cell-containing fluid with the adsorbent, and a nucleated cell fraction is recovered through the outlet. In recovering a nucleated cell fraction through the outlet of the filter, the nucleated cell fraction is preferably recovered through the outlet by introducing a solution for recovering the fraction through the inlet of the filter. Examples of the cells to be removed include granulocytes, monocytes, platelets, B lymphocytes, and lymphocytes having a specific subclass. Examples of the molecules to be removed include low-density lipoproteins, fibrinogen, and β2-microglobulin. Specifically, granulocytes are captured by the filter and removed, and a fraction containing mononuclear cells is recovered.

In cases where an adsorbent filled in the filter has affinity with nucleated cells to be recovered, a cell-containing fluid is first introduced through the inlet of the filter, next cells to be removed or contaminants are allowed to flow out through the outlet, and then a nucleated cell fraction can be recovered through the inlet. In recovering a nucleated cell fraction through the inlet of the filter, the nucleated cell fraction is preferably recovered through the inlet by introducing a solution for recovering the fraction through the outlet of the filter. Examples of the cells to be removed include red blood cells, T lymphocytes, and lymphocytes having a specific subclass. Specifically, stem cells captured by the filter are recovered after unnecessary cells passed through the filter.

Further, when the nucleated cell fraction is recovered by introducing a solution for recovering the fraction through the outlet of the filter, cells to be removed or contaminants are allowed to be efficiently washed away through the outlet by introducing a wash solution from the inlet of the filter before the fraction is recovered. The wash solution is not particularly limited as long as it can wash only cells to be removed or contaminants away. Examples of the wash solution include physiological saline, a Ringer's solution, mediums used for cell culture, common buffer solutions such as a phosphate buffer, and solutions prepared by adding serum or protein to these solutions and buffers.

Further, after a cell-containing fluid or wash solution is introduced from the inlet of the filter, and cells to be removed or contaminants are allowed to be removed through the outlet, the partition may be removed or the area of the opening of the partition may increase. By recovering the nucleated cell fraction after such operations, improvement in recovery yield of the nucleated cell is promising.

The recovery solution is favorably used in order to recover nucleated cells captured in the filter or mononuclear cells left in the filter. Examples of the recovery solution include, but are not particularly limited to, physiological saline; liquids containing a divalent cation such as magnesium ion or calcium ion, a saccharide, a serum, or a protein; buffers, mediums, plasma, and liquids containing these components. In order to enhance the recovery yield of nucleated cells captured by the filter, the viscosity of the recovery solution may be increased. Any material for increasing the viscosity may be added to the recovery solution. Examples of the material include, but are not particularly limited to, albumin, fibrinogen, globulin, dextran, hydroxyethyl starch, hydroxy cellulose, collagen, hyaluronic acid, and gelatin.

The flow rate to pass the cell-containing fluid and the recovery solution, and methods thereof are not particularly limited. Examples of the methods include allowing to flow by gravity, allowing to flow using a roller clamp or syringe pump to maintain the flow rate, and flushing by applying high pressure. In order to recover nucleated cells captured in the filter, in view of the recovery efficiency of the nucleated cells, a method of flushing by applying high pressure is preferred. Further, in order to recover mononuclear cells left in the filter while captured granulocytes are left in the filter, in view of granulocyte removal efficiency, it is preferable to pass the recovery solution through the filter using a syringe pump at a constant flow rate. It is more preferable to pass the recovery solution through the filter using a syringe pump at a flow rate of not higher than 2.5 mL/min because the mononuclear cell fraction can be recovered while more granulocytes are kept on the adsorbent to be captured.

Figure 4:
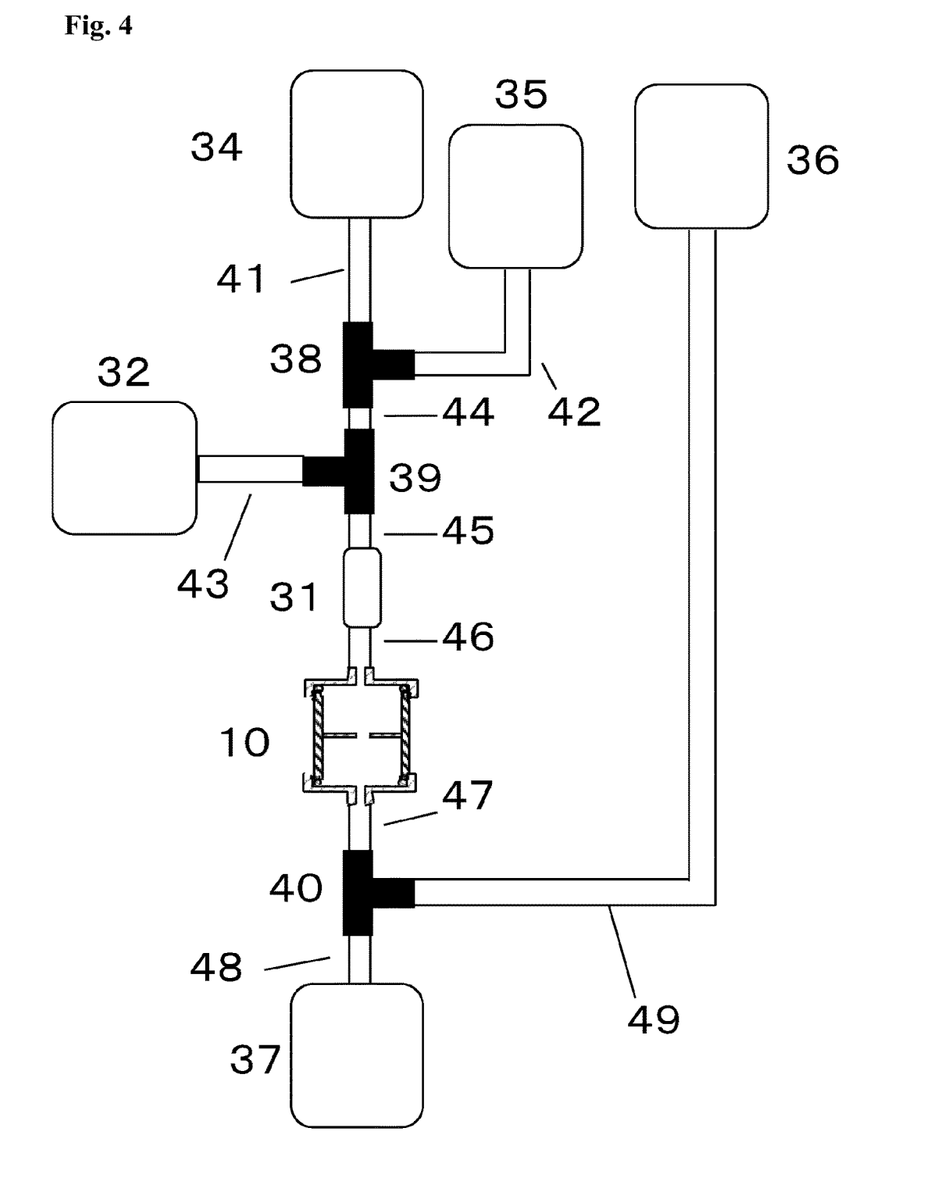
FIG. 4 shows lines which include a cell separation filter.

FIG. 4 illustrates an example of closed lines in which cells are separated using the cell separation filter of the present invention. In the use of such lines, a means for storing a cell-containing fluid is usually placed on the side of the inlet of the filter, and a means for receiving the cell-containing fluid passing through the filter is usually placed on the outlet side. In addition, a means for receiving a recovery solution or a means for receiving a recovery solution passed through the filter is placed on the inlet side or outlet side of the filter. The means for receiving a recovery solution and the means for receiving a recovery solution passed through the filter are selected in consideration where they are to be placed on the inlet side or outlet side of the filter depending on the direction of the flow of the recovery solution.

Further, when priming is performed for the purpose of removing air in the cell separation filter, improving the cell capturing efficiency, and securing paths for blood, a means for storing a priming solution or a means for receiving a priming solution passed through the filter is usually placed on the inlet or on the outlet side of the filter side. The means for storing a priming solution and the means for receiving a priming solution passed through the filter are selected in consideration where they are to be placed on the inlet side of outlet side of the filter depending on the direction of the flow of the priming solution. The means for storing a priming solution and the means for receiving a priming solution passed through the filter may be installed with additional lines formed separately from the lines for the means for storing a cell-containing fluid, or may be replaced with the means for storing a cell-containing fluid. These means are connected to the filter by opening or closing cocks or the like according to the steps in the method for preparing nucleated cells. The lines preferably include a three-way stopcock, a roller clamp, a clamp, or the like in order to control the flows of the solutions.

After recovering the nucleated cell fraction from the cell separation filter, it is preferable that the nucleated cell fraction passes through a dialyzer, and the nucleated cell fraction is recovered.

According to the method for preparing nucleated cells of the present invention, unnecessary molecules can be removed from the cell-containing fluid. Examples of molecules to be removed by the method for preparing nucleated cells of the present invention include low-density lipoproteins, fibrinogen, and β2-microglobulin (β2M).

The mononuclear cell recovery ratio obtained by the method for preparing nucleated cells of the present invention can be calculated by dividing the mononuclear cell recovery yield (M) by the granulocyte recovery yield (G). Here, the mononuclear cell recovery yield (M) refers to the yield of mononuclear cells recovered from the material cell-containing fluid into the nucleated cell fraction. The granulocyte recovery yield (G) refers to the yield of granulocytes recovered from the material cell-containing fluid into the nucleated cell fraction. A higher mononuclear cell recovery ratio indicates higher ability to remove granulocytes. Use of the cell separation filter of the present invention improves the efficiency of capturing granulocytes by the adsorbent, and therefore enables efficient preparation of a mononuclear cell fraction while reducing granulocyte contamination. Therefore, it is preferred that the granulocyte is selectively removed from the cell-containing fluid. The mononuclear cell recovery ratio is preferably not less than 5.3, more preferably not less than 8.3, and still more preferably not less than 25.2. Incases where the mononuclear cell recovery ratio is less than 5.3, the granulocyte contamination comparable to that in use of a conventional cell separation filter is observed. Such mononuclear cells tend to cause side effects when administered to patients. The upper limit of the mononuclear cell recovery ratio is not particularly limited because the ratio has an effect not only on the structure of the cell separation filter but also on the performance of the non-woven fabrics. However, the ratio is preferably not more than 100.

EXAMPLES

The following description is offered to illustrate the present invention in more detail with reference to examples, but the present invention is not limited only to these examples.

Example 1

A container with a height (inner dimension) of 16 mm, a radius (R) of 9 mm, and a cross-sectional area (S2) of a filter of 254 mm$^2$ was used. The space of the container was equally separated into two rooms by a partition provided with one 3-mm-diameter opening (the shortest distance (r) from the center of the opening to the edge of the opening was 1.5 mm) at the center (the container has an area (S1) of the opening of 7.1 mm$^2$ and a distance (T) from the center to the farthest point of the opening from the center of the cross section of 1.5 mm, which was the same as the (r)). Each of the two rooms was filled with 16 pieces of nylon 6 non-woven fabrics (air permeability: 40 mL/cm$^2$/sec, thickness: 0.30 mm, fiber diameter: 16.0 μm) laminated therein. Thus, a cell separation filter was prepared.

Next, a 50-mL syringe was filled with 45 mL of physiological saline as a priming solution. The syringe was connected to the inlet of the filter through a female lock connector. The physiological saline (45 mL) was passed through the filter by pressing a plunger of the syringe slowly.

Then, a 20-mL syringe was filled with 10 mL of swine bone marrow (which was previously anticoagulated with 50 IU/mL of heparin sodium and passed through a 70-μm cell strainer to remove coagulates). The syringe was connected to the inlet of the filter through a porelon tube, and attached to a syringe pump. The swine bone marrow (10 mL) was introduced into the filter at a flow rate of 0.625 mL/min over 16 minutes, and 10 mL of nucleated cells which were discharged from the outlet side was received in a recovery container.

Finally, a 20-mL syringe was filled with 10 mL of physiological saline (a recovery solution), which contained 0.1% magnesium sulfate and 0.1% calcium chloride. The syringe was connected to the inlet of the filter with a porelon tube, and was introduced into the filter at a flow rate of 0.625 mL/min over 16 minutes using a syringe pump, and 10 mL of nucleated cells, which passed through the outlet side, were received in a recovery container. The time from the start of allowing the priming solution to flow to the completion of the recovery of the nucleated cells by allowing a recovery solution to flow was 40 minutes.

The leucocyte concentration in the recovered nucleated cells (20 mL) and the untreated bone marrow were measured with a blood cell counter (K-4500, produced by Sysmex Corp.). Separately, the untreated bone marrow and the recovered nucleated cells were hemolyzed with FACS PharmLyse and then the proportions granulocytes and mononuclear cells were measured with a flow cytometer (FACSCanto, produced by BD). The total number of mononuclear cells was calculated by the following equation based on the leucocyte concentration and the proportions of granulocytes and mononuclear cells.

(Total number of mononuclear cells per 10 ml of untreated bone marrow)=(Leucocyte concentration in untreated bone marrow)×(Proportion of mononuclear cells in leucocytes in untreated bone marrow)×10 [mL]

(Total number of mononuclear cells per 20 ml of recovered nucleated cells)=(Leucocyte concentration of recovered nucleated cells)×(Proportion of mononuclear cells in leucocytes in recovered nucleated cells)×20 [mL]

The mononuclear cell recovery yield [%] was calculated from the total numbers of mononuclear cells before or after the treatment, based on the following equation: (The number of mononuclear cells in recovered nucleated cells)/(The number of mononuclear cells in untreated bone marrow)×100. The mononuclear cell recovery yield was found to be 48%. The total number of granulocytes in the recovered nucleated cells was likewise calculated. The granulocyte recovery yield [%] was also calculated based on the following equation: (The number of granulocytes in recovered nucleated cells)/(The number of granulocytes in untreated bone marrow)×100. The granulocyte recovery yield was found to be 2%. The mononuclear cell recovery ratio was also calculated from the mononuclear cell recovery yield and the granulocyte recovery yield based on the following equation: (Mononuclear cell recovery yield)/(Granulocyte recovery yield). The mononuclear cell recovery ratio was found to be 25.2.

Example 2

A container with a height (inner dimension) of 14 mm, a radius (R) of 9 mm, and a cross-sectional area (S2) of a filter of 254 me was used. The space of the container was equally separated into two rooms by a partition provided with one 2-mm square opening (r=1 mm) at the center (S1=4 mm$^2$, T=1.4 mm). The same procedures as in Example 1 were performed using the container, except that the number of individuals of swines n=1. The time from the start of allowing the priming solution to flow to the completion of the recovery of the nucleated cells by allowing a recovery solution to flow was 40 minutes. The mononuclear cell recovery yield, granulocyte recovery yield, and mononuclear cell recovery ratio per 20 ml of the resulting mononuclear cells were calculated. The results are shown in Table 1.

Example 3

A container with a height (inner dimension) of 14 mm, a radius (R) of 9 mm, and a cross-sectional area (S2) of a filter of 254 mm$^2$ was used. The space of the container was equally separated into two rooms by a partition provided with one 6-mm square opening (r=3 mm) at the center (S1=36 mm$^2$, T=4.2 mm). The same procedures as in Example 1 were performed using the container, except that the number n of individuals of swines=1. The time from the start of allowing the priming solution to flow to the completion of the recovery of the nucleated cells by allowing a recovery solution to flow was 40 minutes. The mononuclear cell recovery yield, granulocyte recovery yield, and mononuclear cell recovery ratio per 20 ml of the resulting mononuclear cells were calculated. The results are shown in Table 1.

Example 4

A container with a height (inner dimension) of 14 mm, a radius (R) of 9 mm, and a cross-sectional area (S2) of a filter of 254 mm² was used. The space of the container was equally separated into two rooms by a partition provided with one 8-mm square opening (r=4 mm) at the center (S1=64 mm², T=5.7 mm). The same procedures as in Example 1 were performed using the container, except that the number n of individuals of swines=1. The time from the start of allowing the priming solution to flow to the completion of the recovery of the nucleated cells by allowing a recovery solution to flow was 40 minutes. The mononuclear cell recovery yield, granulocyte recovery yield, and mononuclear cell recovery ratio per 20 ml of the resulting mononuclear cells were calculated. The results are shown in Table 1.

Example 5

A container with a height (inner dimension) of 14 mm, a radius (R) of 9 mm, and a cross-sectional area (S2) of a filter of 254 mm² was used. The space of the container was equally separated into two rooms by a partition provided with four 2-mm square openings (r=1 mm) within a 5.8-mm radius circle of the center of the partition (S1=16 mm², T=5.8 mm). The same procedures as in Example 1 were performed using the container, except that the number n of individuals of swine=1. The time from the start of allowing the priming solution to flow to the completion of the recovery of the nucleated cells by allowing a recovery solution to flow was 40 minutes. The mononuclear cell recovery yield, granulocyte recovery yield, and mononuclear cell recovery ratio per 20 ml of the resulting mononuclear cells were calculated. The results are shown in Table 1.

Comparative Example 1

The same procedures as in Example 1 were performed using a container with a height (inner dimension) of 16 mm, a diameter (inside diameter) of 18 mm (R=9 mm, S2=254 mm²), which had no partition. The time from the start of allowing the priming solution to flow to the completion of the recovery of the nucleated cells by allowing a recovery solution to flow was 40 minutes. The mononuclear cell recovery yield, granulocyte recovery yield, and mononuclear cell recovery ratio per 20 ml of the resulting mononuclear cells were calculated. The results are shown in Table 1.

(Comparative Example 2) Preparation of Mononuclear Cells by Ficoll-Paque Fractionation Fresh swine bone marrow (2 mL) anticoagulated with heparin was combined and diluted with physiologic saline (2 mL). Next, Ficoll Paque-Plus solution (3 mL) (GE Healthcare Japan) was added to a 15-mL centrifuge tube, and the bone marrow diluted as described above was layered on the Ficoll solution. The solution was centrifuged with a centrifugal separator at 400 g of rotation speed for 30 minutes to recover a mononuclear cell fraction. In order to remove the Ficoll solution, the recovered mononuclear cell fraction was combined with physiologic saline (10 mL), and the mixture was centrifuged with a centrifugal separator at 450 g of rotation speed for 10 minutes to remove the supernatant. The remaining fraction was again combined with physiologic saline (10 mL), and then the mixture was centrifuged at 450 g of rotation speed for 10 minutes to remove the supernatant again. Physiological saline was added to the remaining fraction such that the total fluid volume should be 1 mL. The mononuclear cell recovery yield, granulocyte recovery yield, and mononuclear cell recovery ratio of the resulting solution were calculated in the same manner as in Example 1. The results are shown in Table 1. Although almost the same mononuclear cell recovery yield and granulocyte recovery yield as those of Example 2 were obtained, unfortunately the process is time-consuming for centrifugation and the like. Also, the process is disadvantageous in that the process requires complicated operations, shows high inter-operator variability, and requires operations in an open system.

TABLE 1

| | Number of partition | Number of opening of partition | S1/S2 | T/R | r/R | Mononuclear cell recovery yield [%] | Granulocyte recovery yield [%] | Mononuclear cell recovery ratio | Treating time [min] |
|---|---|---|---|---|---|---|---|---|---|
| Example 1 | 1 | 1 | 0.027 | 0.17 | 0.17 | 48 | 2 | 25.2 | 40 |
| Example 2 | 1 | 1 | 0.016 | 0.16 | 0.11 | 53 | 9 | 5.7 | 40 |
| Example 3 | 1 | 1 | 0.14 | 0.47 | 0.33 | 51 | 6 | 8.3 | 40 |
| Example 4 | 1 | 1 | 0.25 | 0.63 | 0.44 | 57 | 8 | 6.8 | 40 |
| Example 5 | 1 | 4 | 0.063 | 0.64 | 0.11 | 54 | 10 | 5.3 | 40 |
| Comparative Example 1 | 0 | — | — | — | — | 33 | 8 | 4.1 | 40 |
| Comparative Example 2 | — | — | — | — | — | 41 | 5 | 8.2 | 80 |

Table 1 clearly shows that installation of the partition separating the non-woven fabrics in the filter improved the recovery yield of the nucleated cells and reduced unnecessary cell contamination, although the non-woven fabrics are designed identically in all the Examples and Comparative Examples. As shown in Comparative Example 2, recover of cells in accordance with the present invention needed only half the time the centrifugation takes to recover cells, and achieved the same or higher recovery yield and unnecessary cell contamination than those obtained by centrifugation. Accordingly, it was recognized that nucleated cells could be efficiently recovered easily in a closed system.

REFERENCE SIGNS LIST

10 Cell separation filter
11 Container
12 Partition
13 Inlet
14 Opening of the partition
15 Outlet 16 Adsorbent
17 Center of the cross-section of the filter
18 Edge of the container
19 Point at the opening of the partition furthest from the center of the cross section of the filter
20 Center of the opening of the partition
31 Chamber
32 Means for storing priming solution flowing through cell separation filter
34 Means for storing a cell-containing fluid
35 Means for receiving a recovery solution
36 Means for storing a priming solution
37 Means for receiving cell-containing fluid and recovery solution flowing through cell separation filter
38 to 40 Three-way stopcocks
41 to 49 Lines

The invention claimed is:

1. A cell separation filter comprising:
a container having an inlet and an outlet,
an adsorbent filled in the container, and
a partition having an opening for separating the adsorbent, the container being divided into two or more rooms by the partition.

2. The cell separation filter according to claim 1, wherein a value (S1)/(S2) is not less than 0.006 and not more than 0.44, where (S1) is an area of the opening of the partition, and (S2) is a cross-sectional area of the filter.

3. The cell separation filter according to claim 2, wherein (S1) is 1.2 to 625 mm² and/or (S2) is 75 to 2500 mm².

4. The cell separation filter according to claim 3, wherein a value (T)/(R) is not less than (r)/(R) and not more than 0.79, where (R) is the shortest distance from the center to the edge of the container in the cross-section of the filter, (T) is the farthest distance from the center to the edge of the opening of the partition in the cross-section of the filter, and (r) is the shortest distance from the center of the opening to the edge of the opening.

5. The cell separation filter according to claim 3, wherein the adsorbent is composed of non-woven fabrics.

6. The cell separation filter according to claim 2, wherein a value (T)/(R) is not less than (r)/(R) and not more than 0.79, where (R) is the shortest distance from the center to the edge of the container in the cross-section of the filter, (T) is the farthest distance from the center to the edge of the opening of the partition in the cross-section of the filter, and (r) is the shortest distance from the center of the opening to the edge of the opening.

7. The cell separation filter according to claim 2, wherein the adsorbent is composed of non-woven fabrics.

8. The cell separation filter according to claim 1, wherein a value (T)/(R) is not less than (r)/(R) and not more than 0.79, where (R) is the shortest distance from the center to the edge of the container in the cross-section of the filter, (T) is the farthest distance from the center to the edge of the opening of the partition in the cross-section of the filter, and (r) is the shortest distance from the center of the opening to the edge of the opening.

9. The cell separation filter according to claim 1, wherein the adsorbent is composed of non-woven fabrics.

10. The cell separation filter according to claim 1, wherein the adsorbent is composed of porous cellulose particles.

11. The cell separation filter according to claim 10, wherein the adsorbent comprises a compound having a log P value of not less than 2.50 immobilized on the porous cellulose particles, wherein P is an octanol-water partition coefficient.

12. The cell separation filter according to claim 10, wherein the adsorbent comprises a tryptophan derivative and a polyanionic compound immobilized on the porous cellulose particles.

13. A method for preparing nucleated cells comprising the steps of:
(a) introducing a cell-containing fluid through the inlet of the cell separation filter according to claim 1 to contact the cell-containing fluid with the non-woven fabrics; and
(b) recovering a nucleated cell fraction from the cell separation filter.

14. The method according to claim 13, wherein, in the step (b), the nucleated cell fraction is recovered by introducing a solution for recovering the fraction through the inlet of the filter.

15. The method according to claim 13, wherein, in the step (b), the nucleated cell fraction is recovered by introducing a solution for recovering the fraction through the outlet of the filter.

16. The method according to claim 13, further comprising after the step (b):
passing the nucleated cell fraction through a dialyzer; and recovering the nucleated cell fraction.

17. The method according to claim 13, wherein the nucleated cell fraction is a mononuclear cell fraction.

18. The method according to claim 13, wherein granulocytes are selectively removed from the cell-containing fluid.

19. The method according to claim 13, wherein at least one selected from the group consisting of low-density lipoproteins, fibrinogen, and β2-microglobulin (β2M) is removed from the cell-containing fluid.

20. The method according to claim 18, wherein a value (M)/(G) is not less than 5.3, where (M) is a recovery yield of mononuclear cells, and (G) is a recovery yield of the granulocytes.

* * * * *